United States Patent [19]
Rydell

[11] Patent Number: 5,171,255
[45] Date of Patent: Dec. 15, 1992

[54] BIOPSY DEVICE

[75] Inventor: Mark A. Rydell, Golden Valley, Minn.

[73] Assignee: Everest Medical Corporation, Minneapolis, Minn.

[21] Appl. No.: 774,892

[22] Filed: Oct. 11, 1991

[51] Int. Cl.$^5$ .............................................. A61B 17/39
[52] U.S. Cl. ................................... 606/170; 606/171
[58] Field of Search ............ 606/170, 167, 174, 171, 606/110, 112, 115; 604/22

[56] References Cited

U.S. PATENT DOCUMENTS

| | | | |
|---|---|---|---|
| 3,173,414 | 3/1965 | Guillant | 606/171 X |
| 3,837,345 | 9/1974 | Matar | 606/171 X |
| 4,669,469 | 6/1987 | Gifford, III et al. | 606/170 X |
| 4,678,459 | 7/1987 | Onik et al. | 604/22 |
| 4,950,278 | 8/1990 | Sachse et al. | 606/170 |
| 4,961,430 | 10/1990 | Sheahon | 606/171 X |
| 5,026,383 | 6/1991 | Nobles | 606/170 X |
| 5,085,659 | 2/1992 | Rydell | 606/48 X |

Primary Examiner—Peter A. Aschenbrenner
Attorney, Agent, or Firm—Haugen and Nikolai

[57] ABSTRACT

A biopsy instrument comprises an elongated flexible tube having a sharpened metal sleeve affixed to its distal end. An anvil member is affixed to the distal end of an elongated rod or wire which fits through the lumen of the tube and which is reciprocally moveable in the longitudinal direction by appropriately manipulating a handle device affixed to the proximal end of the tube. Affixed to the anvil member and electrically connected to the rod is an electrode. Means are provided for connecting an RF voltage between the electrode and metal sleeve for coagulating blood at the site where a tissue sample is excised from the internal wall of a body organ. The tissue sample is excised by positioning it against the sharpened edge of the metal sleeve and drawing back on the anvil to sever the sample and draw it into the interior of the sleeve where it remains until removed.

6 Claims, 2 Drawing Sheets

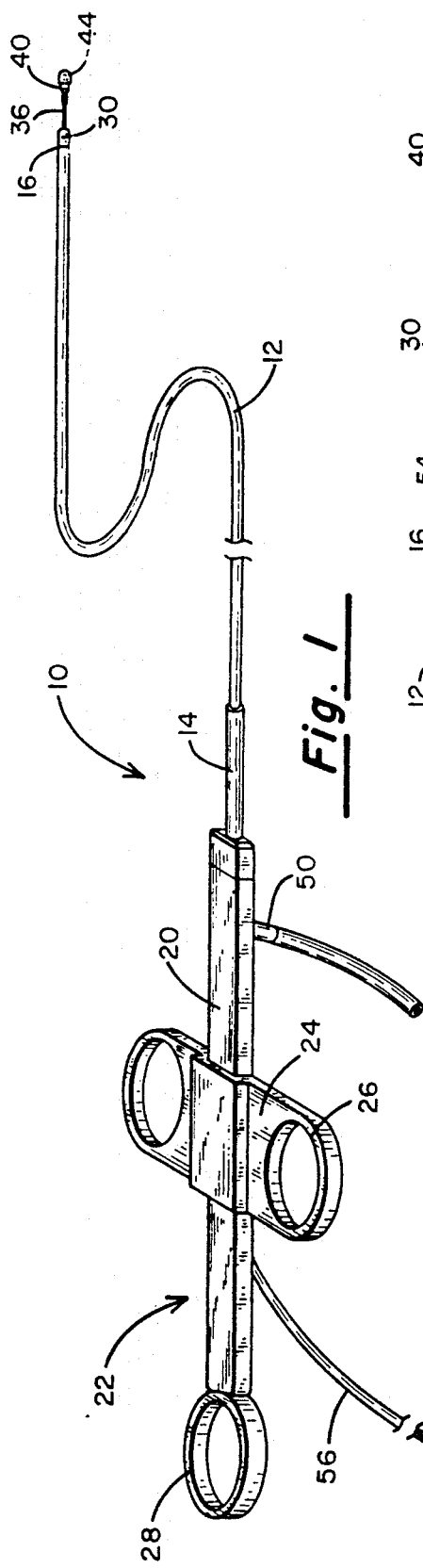
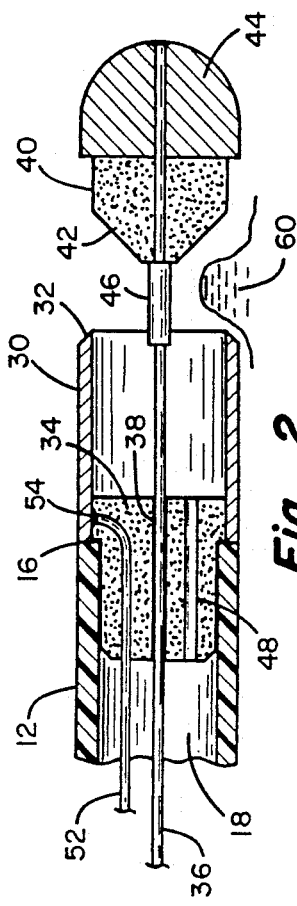
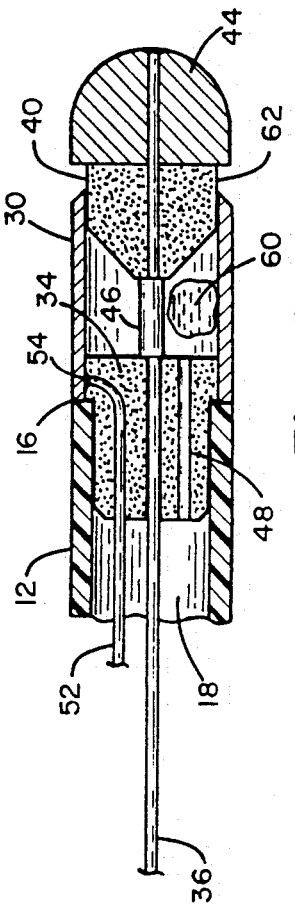

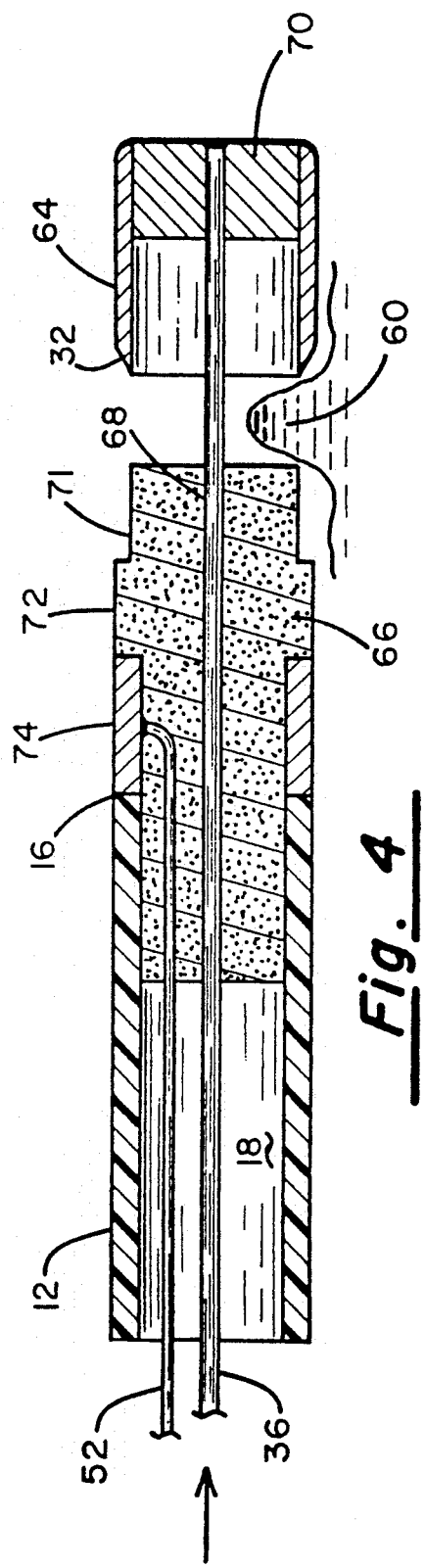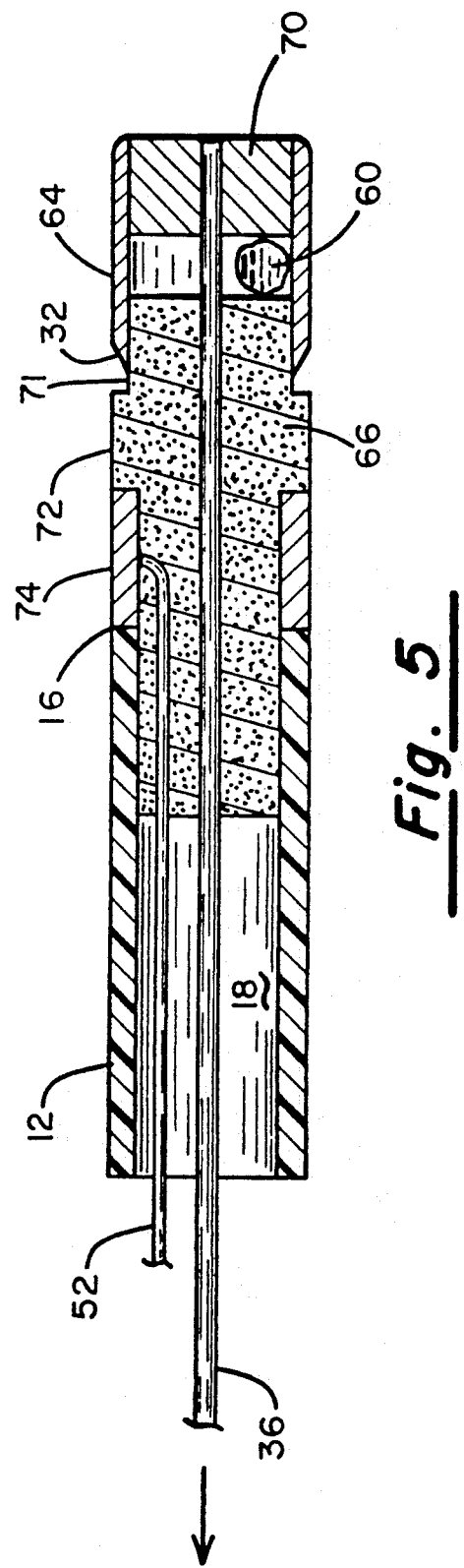

BIOPSY DEVICE

This application is a continuation of application Ser. No. 07/616,562, filed Nov. 21, 1990, now U.S. Pat. No. 5,085,659.

BACKGROUND OF THE INVENTION

I. Field of the Invention

This invention relates generally to tissue biopsy apparatus, and more particularly to a biopsy instrument which may be used in combination with an endoscope for excising suspicious tissue samples from an interior wall of an internal organ and which incorporates a pair of bipolar electrodes at the distal end thereof for subsequently coagulating bleeding blood vessels following excision of the tissue sample.

Discussion of the Prior Art

The prior art device over which the present invention is deemed to be an improvement comprises an elongated tube having a reciprocally moveable control rod extending through the lumen thereof and affixed at its distal end are tiny clamshell-like tongs which can be made to open and close when a lever mechanism at the proximal end of the elongated tube is manipulated. The device is dimensioned to pass through an endoscope and, in use, the clamshell tongs, in their open disposition, are made to approach the vessel wall in a perpendicular direction at the location where the tissue sample is to be excised. Then, by manipulating the handle at the proximal end of the instrument, the tongs are made to close on the sample which is pinched and partially cut by the edges of the clamshell tongs. As skilled surgeons will appreciate, when a vessel wall is approached from the perpendicular direction, the chances for perforation of that vessel wall are considerably greater than when the approach is made at a 0° angle relative to the wall.

The prior art instrument over which the present invention is deemed to be an improvement also provides, it is monopolar, thereby requiring a large area body electrode positioned at a location on the skin surface quite remote from the site of the biopsy. The coagulating current is applied between the clamshell tip on the biopsy instrument and the body plate and, again, the risk of perforation is increased by virtue of the monopolar electrode configuration employed.

Another drawback of the above-described prior art biopsy instrument is that the tissue sample is held between the closed clamshell halves and during electrocautery, the sample may be destroyed by the high temperatures to which it is exposed. This may preclude a pathologist from accurately determining the nature of the cells contained in the excised sample.

The prior art instrument can only be used to remove a single sample from the vessel wall without having to first remove the instrument from the endoscope and then reinsert it to gather a second sample. This is due to the fact that after a first sample is excised and held in the jaws of the clamshell, it will be lost when the clamshell is reopened in an attempt to excise the second sample.

The linkage mechanism affixed to the distal end of the elongated tube for operating the clamshell halves is difficult to assemble which significantly increases the cost of the instrument. In fact, the cost is too high to allow the instrument to be considered as a practical single-use or disposable instrument.

OBJECTS

It is accordingly an object of the present invention to provide an improved biopsy instrument for excising tissue samples from the interior wall of a hollow body organ;

Another object of the invention is to provide a biopsy device of the type described which includes a mean for coagulating blood at the site of the excision.

A further object of the invention is to provide an improved biopsy device for excising tissue samples from the interior wall of a hollow body organ where the tissue sample is approach at a 0° angle relative to the wall surface on which the sample is growing.

Another object of the invention is to provide an improved biopsy instrument of the type described in which a bipolar electrode system is used for coagulation.

Still another object of the invention is to provide a biopsy instrument for removing tissue samples from the interior wall of a hollow body organ and which includes bipolar electrocautery electrodes configured such that the heat produced for coagulation does not destroy the tissue sample.

Yet another object of the invention is to provide an improved biopsy instrument which may be introduced through an endoscope and used to successively remove one or more tissue samples from the interior wall of a hollow body organ without having to retract the instrument from the endoscope between each sample.

A yet further object of the invention is to provide an improved biopsy device for removing tissue samples from a hollow internal organ which is sufficiently simple in its construction so as to be disposable from an economic standpoint.

SUMMARY OF THE INVENTION

The foregoing objects and advantages of the invention are achieved by providing a biopsy instrument comprising an elongated tube having a proximal end, a distal end and a lumen extending therebetween, the outside diameter of the tube being sufficiently small to readily pass through an endoscope. Extending through the lumen of the tube is a first wire or rod which is reciprocally moveable and a second wire which remains stationary. The stationary wire is connected at its distal end to an annular cutter in the form of a tubular ring or sleeve made from stainless steel or another suitable metal. The distal edge of the cutter is honed to the sharpness of a surgical scalpel. Fitted onto the distal end of the reciprocally moveable wire or rod is an insulating anvil whose outside dimension allows it to fit within the central opening in the annular cutter with a close tolerance. The anvil terminates in a conductive metal dome. This dome is electrically joined to the reciprocally moveable wire or rod and forms, with the conductive cutter, a pair of bipolar electrodes. When the biopsy device is inserted through an endoscope and allowed to project out its distal end, the anvil is initially in its retracted condition relative to the cutter and, hence, the sharpened edge of the cutter is shielded to prevent inadvertent cutting of tissue. As the surgical field is viewed through the endoscope, the ring cutter is positioned just proximal of the tissue sample and then the handle is manipulated to extend the anvil distal of the sample. When so positioned, the handle is then manipulated to draw the anvil back against and into the cutter, shearing off the tissue sample and storing it within the annular cutter. Any bleeding caused by the cutting can now be coagulated by applying a RF voltage across the bipolar electrodes (the ring and metal dome) while moving the instrument back and forth across the site of the excision.

DESCRIPTION OF THE DRAWINGS

The foregoing features, objects and advantages of the invention will become apparent to those skilled in the art from the following detailed description of a preferred embodiment, especially when considered in conjunction with the accompanying drawings in which like numerals in the several views refer to corresponding parts.

FIG. 1 is a perspective view of the biopsy instrument in accordance with the present invention;

FIG. 2 is a greatly enlarged cross-sectional view of the distal end portion of the instrument of FIG. 1 with the anvil extended; and FIG. 3 is a greatly enlarged cross-sectional view of the distal end portion of the instrument of FIG. 1 with the anvil member shown retracted into the cutting sleeve.

FIGS. 4 and 5 are a partial cross-sectional view of the distal end portion of the biopsy device in accordance with an alternative embodiment, and

DESCRIPTION OF THE PREFERRED EMBODIMENT

Referring to FIG. 1, there is shown a perspective view of a biopsy device primarily intended for use in the gastrointestinal tract for gathering tissue samples for later pathological examination. The device is indicated generally by numeral 10 and is seen to include an elongated flexible plastic tube or sheath 12 having a proximal end 14, a distal end 16 and a lumen 18 running therebetween. The proximal end of the tube 12 is affixed to a stationary portion 20 of a handle assembly 22. The handle 22 preferably comprises a device as is set forth in applicant's co-pending application Ser. No. 590,783, filed Oct. 1, 1990 and entitled "IMPROVED HANDLE FOR POLYPECTOME SNARE WITH BIPOLAR ELECTRODES" now Pat. No. 5,026,311. As is explained in that application, the handle device includes a longitudinally displaceable slide block disposed in a longitudinal slot formed in the stationary member 20, the slide block being attached to a transversely extending wing member 24 having two finger receiving openings 26 formed therein. Also affixed to the stationary member 20 is a thumb-receiving ring 28 which allows the physician to readily grasp the handle and manipulate the slide 24 back and forth in the longitudinal direction.

As can also be seen in FIG. 1, and perhaps more clearly in the enlarged distal end views of FIGS. 2 and 3, there is affixed to the distal end of the tube 12 a metal ring or sleeve 30 which is beveled at its distal edge 32 to form a sharp cutting edge. To facilitate the attachment of the metal sleeve 30 to the distal end 16 of the tube 12, it has been found convenient to provide an insulating plug 34 which may be fabricated from a suitable plastic, such as medical-grade polysulfone. Alternatively, the plug 34 may be formed from a ceramic, such as aluminum oxide or other ceramic. The plug 34 is fitted into the distal end of the tube and held in place by a suitable adhesive. The metal sleeve 30 may then be crimped or adhesively bonded onto a portion of the plug 34 extending outward from the distal end 16 of the tube 12.

Extending through the lumen 18 of the device 10 is an elongated rod or conductor 36 whose proximal end is fitted into the slide block of the handle assembly 22 in the manner disclosed in the above-captioned pending application and whose distal end extends through a longitudinal bore 38 formed in the plug 34. When the member 24 is advanced in the distal direction, the end of the rod 36 projects in the distal direction beyond the beveled edge 32 of the sleeve 30. Secured to the distal end portion of the rod 36 is an insulative (plastic or ceramic) anvil member 40 whose outer diameter is only slightly less than the internal diameter of the metal sleeve 30. The proximal end of the anvil member 40 is preferably beveled as at 42 to facilitate its entrance into the sleeve 30 when the slide assembly 24 is moved in the proximal direction (see FIG. 3).

Bonded or otherwise affixed to the forward or distal end of the anvil 40 is a dome-shaped metal electrode 44. As is apparent from the enlarged views of FIGS. 2 and 3, the metal electrode member 44 is in electrical contact with the rod 36 which extends the length of the tubular member 12. A short length of insulation 46 covers the rod 36 at a location just proximal of the anvil member 40 and, in practice, may either comprise an insulating coating directly on the wire 36 or a piece of heat-shrink tubing whose outside diameter is larger than that of the bore 38 formed in the plug 34. The length of the insulating member 46 allows a portion of the anvil 40 to slide into the sleeve 30 while still acting as a stop to prevent the anvil from totally entering the sleeve 30 and abutting the front face of the plug 34.

It is also to be noted in FIGS. 2 and 3 that the plug 34 includes a further bore or passageway 48 extending longitudinally therethrough. This passage is intended to allow a fluid, e.g., pressurized air or a liquid injected through a flushing port 50 in the handle assembly 22 and flowing through the lumen 18 of the tube 12 to dislodge a collected tissue sample, all as will be further described hereinbelow.

A conductive wire 52 extends through the lumen 18 of the tube 12 and is electrically connected at its distal end, at 54, to the metal sleeve 30. Connected to the proximal end of the wire 52 and the conductive rod 36 is an electrical lead 56 which enters the handle assembly 22 and has its wires crimped to the conductors 52 and 36 in the manner described in the aforereferenced application. The leads 56 include plug-type connectors 58 allowing the biopsy instrument of the present invention to be connected to an electrosurgical generator whereby a predetermined RF voltage may be applied. A suitable electrosurgical generator for use with the biopsy instrument of the present invention is disclosed in the Stasz et al. U.S. Pat. No. 4,903,696.

For purposes of example only and with no limitation intended, the tube 12 may be formed from a variety of plastic materials, including polyethylene, polyester, Teflon ®, etc. The tubing 12 may have an outside diameter of 0.090 in. and an internal diameter of 0.060 in. The sleeve 30 may be formed from 13 gauge stainless steel tubing and, as such, will have an outside diameter of 0.091 in. and an internal diameter of 0.081 in. The length of the sleeve 30 may be about 0.015 in. The plug 34 may have a diameter of 0.065 in. for that portion thereof which fits into the tube 12. The portion supporting the sleeve 30 will preferably have an outside diameter of 0.080 in., allowing it to fit within the sleeve 30. The bore 38 for accommodating the rod 36 may be 0.0145 in. diameter.

The portion of the anvil 40 adapted to fit within the sleeve 30 may be approximately 0.065 in. in length and will have an O.D. of 0.078 in. A 10° bevel on the proximal edge facilitates its ability to fit within the sleeve 30 when the handle assembly 22 is appropriately manipulated. The length of the insulator 46 should be 0.062 in. with the dimensions of the other parts as previously indicated.

Having described the physical features of the biopsy instrument of the present invention, consideration will next be given to its mode of use.

OPERATION

The instrument 10 of the present invention, when used to remove and capture immature polyps on the internal wall of the colon, will be inserted through the lumen of a viewing endoscope and advanced to the location of the immature polyp. Once so positioned, the surgeon will manipulate the handle 22 by advancing the slide 24 in the distal direction, causing the anvil and its attached electrodes 40-44 to move out of the sleeve 30 and across the tissue sample 60 (FIG. 2). The beveled end 32 of the ring-shaped cutter 30 will remain proximal of the tissue sample 60 to be removed. Once the anvil and sleeve are appropriately positioned as indicated, the physician will move the slide 24 in the proximal direction, tensioning the rod 36 and pulling the anvil 40 toward and against the sharpened edge 32 of the sleeve 30. The tissue sample 60 will be forced against the sharp cutting edge and excised. As the anvil is retracted into the sleeve, the tissue sample will also be drawn into the sleeve and captured there. Any remaining polypoid tissue can be eradicated, and bleeding caused by the excision of the tissue sample can now be coagulated by activating the electrosurgical generator and applying an RF voltage across the leads 56 which connect to the conductors 36 and 52 leading to the movable electrode 44 and the stationary cutter sleeve 30, respectively. The sleeve along with electrode 44 form a bipolar pair and when the gap 62 between the two is wiped across bleeding blood vessels, coagulation and hemostasis takes place. Because the insulator 46 surrounds the rod 36, the tissue sample 60 is prevented from touching both the sleeve 30 and the rod 36 during cauterization and, hence, is not exposed to the RF voltage which might otherwise destroy the sample.

In that the tissue sample is firmly contained within the central opening of the ring cutter, the instrument can be repositioned relative to another sample and the removal/cauterization steps repeated. Hence multiple samples can be gathered before extracting the instrument 10 from the endoscope.

The instrument can now be withdrawn from the endoscope and with the slide 24 pushed in the distal direction, the distal end of the sleeve 30 is no longer blocked. If the tissue sample 60 will not fall out with shaking, a syringe full of an appropriate fluid can be connected to the flushing port 50 on the handle assembly 22 and when squeezed, the pressurized fluid will flow through the lumen 18 of the instrument and through the bore 48 formed in the plug 34 to dislodge tissue sample 60 into an appropriate container.

ALTERNATIVE EMBODIMENT

Referring now to FIGS. 4 and 5, there is shown an alternative embodiment of the present invention. Rather than having the tubular cutting blade 30 mounted as the stationary member on the distal end of the flexible plastic tube 12 as in the embodiment of FIGS. 1 through 3, in this alternative arrangement, the metal tubular blade 64 is made movable while the anvil 66 is fixedly attached to the distal end 16 of the flexible tube 12. More particularly, the longitudinally movable rod 36 extends through a bore 68 formed in the anvil 66 and secured to the distal end of the rod is a metal disk 70. Surrounding the disk 70 and conductively joined thereto is the tubular blade 64 having its sharpened beveled edge 32 facing the anvil 66. The outside diameter of the anvil in the portion identified by numeral 71 is slightly less than the internal diameter of the sleeve 64 such that when the rod 36 is pulled in the proximate direction, the portion 70 will enter the sleeve with a close tolerance. It also includes a segment 72 of slightly larger diameter which thereby creates a shoulder stop to limit the extent to which the portion 71 may be inserted into the chamber or cavity within the sleeve 64.

Located just proximal of the segment 72 is a ring electrode 74 which is bonded or otherwise affixed to the anvil member 66. An elongated flexible conductor 52 extends through the lumen 18 of the tube 12 and through a bore formed in the anvil member 66 allowing the distal end thereof to be welded and, therefore, electrically joined to the ring electrode 74. A handle member like that shown in FIG. 1 will be attached to the proximal end of the tube 12 and appropriately attached to the rod 36 so that manipulation of the slide 24 relative to the member 20 will allow the metal sleeve 64 to be moved from the position shown in FIG. 4 to that shown in FIG. 5. In doing so, the tissue segment to be examined identified by the numeral 60 is sheared off by the honed edge 32 of the sleeve 64 and captured within the interior of that sleeve as shown in FIG. 5. Again, when cauterization is desired, an appropriate RF voltage is applied between the conductive rod 36 and the wire 52 causing an arc to form between the bipolar electrodes including the metal sleeve 64 and the ring electrode 74.

This invention has been described herein in considerable detail in order to comply with the Patent Statutes and to provide those skilled in the art with the information needed to apply the novel principles and to construct and use such specialized components as are required. However, it is to be understood that the invention can be carried out by specifically different equipment and devices, and that various modifications, both as to the equipment details and operating procedures, can be accomplished without departing from the scope of the invention itself.

What is claimed is:

1. A biopsy instrument comprising:
   (a) an elongated tube having a proximal end, a distal end having an annular edge beveled to a sharp edge, and a lumen extending from said proximal end to said distal end;
   (b) an elongated longitudinally movable rod extending through said lumen from said proximal end of said tube and beyond said distal end of said tube;
   (c) an anvil member affixed to said rod having a distal end and a proximal end having an outer dimension adapted to fit within said tube with a close tolerance wherein said proximal end of said anvil has a beveled proximal edge tapering toward said rod; and
   (d) means mounted on said rod for imparting longitudinal movement to said anvil for drawing said anvil into said tube or displacing said anvil out of said tube.

2. The biopsy instrument as in claim 1 and further including means for injecting a fluid into the proximal end of said tube and through said lumen to flush the interior of said tube.

3. The biopsy instrument as specified in claim 1 wherein said distal end of said anvil has a greater outer dimension then the outer dimension of said proximal end of said anvil to form a shoulder.

4. The biopsy instrument as specified in claim 1 wherein said tube comprises a flexible plastic material.

5. A biopsy instrument, comprising:
    (a) an elongated member having a proximal end, a distal end and a lumen extending therebetween, said distal end having an outer dimension;
    (b) an elongated longitudinally movable rod extending through said lumen from said proximal end of said member and beyond said distal end of said member;
    (c) an anvil member affixed to said rod and having a proximal end having an annular edge beveled to a sharp edge, said sharp edge having an outer dimension adapted to fit about said distal end of said member with a close tolerance; and
    (d) means mounted on said rod for imparting longitudinal movement to said anvil for drawing said sharp edge of said anvil about said distal end of said member.

6. The biopsy instrument as specified in claim 5 wherein said distal end of said member has a shoulder defining an adjacent portion of said member having an outer dimension greater than the outer dimension of said distal edge of said member.

* * * * *

UNITED STATES PATENT AND TRADEMARK OFFICE
CERTIFICATE OF CORRECTION

PATENT NO. : 5,171,255
DATED : December 15, 1992
INVENTOR(S) : Mark A. Rydell

It is certified that error appears in the above-identified patent and that said Letters Patent is hereby corrected as shown below:

In column 8, line 5, the phrase

"having an outer dimension"

should be deleted.

Signed and Sealed this

Fifth Day of April, 1994

Attest:

BRUCE LEHMAN

*Attesting Officer*     *Commissioner of Patents and Trademarks*